United States Patent
Conti

(10) Patent No.: US 6,946,826 B2
(45) Date of Patent: Sep. 20, 2005

(54) APPARATUS FOR THE DETECTION AND MEASUREMENT OF PARTICULATES IN MOLTEN METAL

(75) Inventor: Richard F. Conti, New Hope, PA (US)

(73) Assignee: Heraeus Electro-Nite International N.V., Houthalen (BE)

( * ) Notice: Subject to any disclaimer, the term of this patent is extended or adjusted under 35 U.S.C. 154(b) by 83 days.

(21) Appl. No.: 10/719,052

(22) Filed: Nov. 21, 2003

(65) Prior Publication Data

US 2004/0201371 A1 Oct. 14, 2004

Related U.S. Application Data

(60) Provisional application No. 60/428,004, filed on Nov. 21, 2002.

(51) Int. Cl.⁷ .............................................. G01N 27/00
(52) U.S. Cl. ...................................................... 324/71.4
(58) Field of Search ........................ 73/865.5; 204/408; 324/71.1, 71.4

(56) References Cited

U.S. PATENT DOCUMENTS

| 3,709,040 | A | 1/1973 | Coe |
| 4,555,662 | A | 11/1985 | Doutre |
| 4,600,880 | A | 7/1986 | Doutre |
| 4,763,065 | A | 8/1988 | Hachey |
| 5,039,935 | A | 8/1991 | Hachey |
| 5,163,997 | A | 11/1992 | Sherwood |
| 5,198,749 | A | 3/1993 | Guthrie |
| 5,241,262 | A | 8/1993 | Guthrie |
| 5,448,923 | A | 9/1995 | Hackett |
| 5,789,910 | A | 8/1998 | Guthrie |
| 5,834,928 | A | * 11/1998 | Doutre ...................... 324/71.4 |
| 6,603,296 | B2 | 8/2003 | Conti |

FOREIGN PATENT DOCUMENTS

| EP | 0 398 719 A2 | 11/1990 |
| EP | 1422510 A1 | * 5/2004 |
| FR | 2208523 A | 6/1974 |

* cited by examiner

*Primary Examiner*—Jay Patidar
*Assistant Examiner*—Walter Benson
(74) *Attorney, Agent, or Firm*—Akin Gump Strauss Hauer & Feld, LLP

(57) ABSTRACT

A probe to measure particulates suspended in molten metal includes an inner tube forming a receiving chamber. The tube includes an orifice permitting molten metal to flow into the chamber. A gas passageway extends out of the tube for connection to a vacuum source. A first electrode including a first member extends into the chamber. A second electrode surrounds a portion of the tube. The first and second electrodes connect to a measurement device for measuring changes in the electrical potential produced by particulates passing through the orifice. A liquidus depressing material within the chamber lowers the liquidus temperature of the molten metal and permits a longer period for measuring particulates therein. A second member is connected to the gas passageway at a first end of the second member. A chill block spaced from the liquidus depressing material is attached to a second end of the second member.

11 Claims, 3 Drawing Sheets

APPARATUS FOR THE DETECTION AND MEASUREMENT OF PARTICULATES IN MOLTEN METAL

CROSS-REFERENCE TO RELATED APPLICATIONS

This application claims the benefit of U.S. Provisional Patent Application No. 60/428,004 filed Nov. 21, 2002, and entitled "Improved Apparatus for the Detection and Measurement of Particulates in Molten Metal," the entire disclosure of which is hereby incorporated herein by reference.

The present application is an improvement upon the apparatus described in U.S. Pat. No. 6,603,296 B2, issued Aug. 5, 2003, and entitled "Apparatus for the Detection and Measurement of Particulates in Molten Metal", the entire disclosure of which is hereby incorporated herein by reference.

BACKGROUND OF THE INVENTION

The present invention comprises an improvement over the apparatus described in the above-identified issued U.S. patent. Set forth below is a basic description of the probe as described in the issued patent which is provided to facilitate a better understanding of the improvement of the current invention. Referring now to FIGS. 1 and 2, there is shown an embodiment of a probe 10 for detecting and measuring particulates suspended in molten metal.

The probe 10 is generally elongated and cylindrical and includes an insertion end 12 and a connector end 14. The probe connector end 14 is adapted to be secured to a supporting structure (not shown) of type well known to those of ordinary skill in the art and employed for inserting measuring probes into molten metal. The probe 10 comprises an elongated closed end inner tube 16, made of an electrically insulative material, such as quartz, which is capable of withstanding the high temperatures present in a bath of molten steel or other molten metal. The insertion end of the inner tube 16 is closed and the connector end is sealed by a suitable generally cylindrical, electrically insulative plug or seal member 18, which is preferably made of a polymeric material and is secured within the open end of the inner tube 16 utilizing a suitable adhesive 20 to form a gas tight seal. The insertion end of the inner tube 16 forms a molten metal receiving chamber 15. At least one orifice 17 extends through the inner tube 16 proximate to the insertion end to permit molten metal to flow into the molten metal receiving chamber 15 when the probe 10 is inserted into molten metal.

A gas passageway 22 comprised of a generally cylindrical, generally tubular member, extends through the seal member 18 and into at least a portion of the inner tube 16. The gas passageway 22 is preferably formed of an electrically conductive metal, such as steel. At least one and preferably a pair of elongated generally cylindrical members or wires 24 are securely connected (mechanically and electrically) to the gas passageway 22 (preferably by welding, brazing or soldering) and extend along the interior of the inner tube 16, terminating proximate to the insertion end of the inner tube 16. The elongated cylindrical members 24 are formed of an electrically conductive material and, in combination with the gas passageway 22 establish a first electrode extending into the molten metal receiving chamber 15. The inner tube 16 is surrounded by a generally tubular, electrically conductive member 26. The inner dimension of the tubular member 26 is at least slightly greater than the outer dimension of the inner tube 16 so that a small annular space 28 separates the tubular member 26 from the outer surface of the inner tube 16. The tubular member 26 establishes a second electrode outside of the inner tube 16. A spacer 34 is inserted between the insertion end of the tubular member 26 and the inner tube 16 to maintain the annular space 28 and to prevent the insertion end of the inner tube 16 from wobbling and to help prevent breakage of the inner tube 16 during shipping and handling. At least a substantial portion of the tubular member 26 is surrounded by an outer sheath 30 formed of a heat resistant material to provide thermal insulation to the tubular member 26 when the probe 10 is inserted into molten metal.

As best shown in FIG. 2, a portion of the tubular member 26 extends beyond the outer sheath 30, such that when the probe 10 is inserted into molten metal, the tubular member 26 is exposed directly to the molten metal. The insertion end of the inner tube 16 is initially covered by a metal slag cap 36 and a paper cap 38 to protect the inner tube 16 and particularly, the orifice 17 from contamination as the probe 10 is inserted through the slag layer that typically covers molten metals during processing.

In use, the connector end 14 of the probe 10 is adapted to be temporarily connected to a suitable supporting structure (not shown). A valve 42 is connected to a vacuum source 44 and a purge gas source 46. When the valve 42 is in a first position, the vacuum source 44 is in fluid communication with the inner tube 16 through the gas passageway 22 to thereby create a vacuum within the molten metal receiving chamber 15. The creation of a vacuum within the chamber 15 facilitates the flow of molten metal through the orifice 17 and into the chamber 15. When the valve 42 is in a second position, gas from the purge gas source 46 is supplied through the gas passageway 22 to the interior of the inner tube 16 to preclude the flow of molten metal or contaminates through the orifice 17 and into the chamber 15.

When the probe 10 is connected to the supporting structure direct electrical connections are established between the connector end of the gas passageway 22 (first electrode) and the connector end of the tubular member 26 (second electrode) and an external measurement device 48. The measurement device 48 is of a type well known to those of ordinary skill in the art for using the electric sensing zone method to detect and measure particulates suspended in molten metal. When the probe 10 is inserted into molten metal, the measurement device 48 establishes a current path between the first and second electrodes and passing through the orifice 17 for measuring changes in the electrical potential between the first and second electrodes which are produced by the passage of particulates entrained in the molten metal passing through the orifice 17.

A liquidus depressing material 50 is provided within the insertion end of the inner tube 16, proximate to the orifice 17. The liquidus depressing material 50 alloys with the molten metal entering the chamber 15 through the orifice 17 and the resulting alloy has a liquidus temperature which is lower than the liquidus temperature of the molten metal entering the chamber 15. Because the wires 24 are close to the wall of the inner tube 16 the cooling of the liquid metal in the central up-welled area is prevented.

In use, the probe 10 is secured to the supporting structure (not shown), so that the first and second electrodes are electrically connected to the measurement device 48 and so that the gas passageway 22 is in fluid communication with the valve 42. Initially, the valve 42 is in the second position, so that an inert purge gas from the purge gas source 46 flows through the gas passageway 22, into the inner tube 16 and out of the orifice 17.

As the probe 10 is inserted through an upper slag layer and into the molten metal, the paper cap 38 is destroyed and the metal slag cap 36 melts to expose the insertion end of the inner tube 16 and the tubular member 26 to the molten metal. As the molten metal engages the inner tube 16, the orifice 17 is effectively sealed causing an increase in gas pressure of the purge gas which is measured by external instrument (not shown). At this time, the valve 42 is changed to the first position, so that the vacuum source 44 is in fluid communication with the gas passageway 22 and the interior of the inner tube 16 to effectively create a vacuum within the chamber 15, thereby causing the molten metal to flow through the orifice 17 and into the chamber 15. As soon as the molten metal engages the wires 24, a complete electrical circuit is established and the measurement device 48 causes current to flow between the electrodes and passing through the orifice 17 for measuring changes in the electrical potential between the electrodes produced by the passage of particulates entrained in the molten metal as they pass through the orifice 17.

The detection and measuring process continues until the chamber 15 is filled with liquid metal and the level of the liquid metal effectively blocks the insertion end of the gas passageway 22 to preclude further vacuum pressure in the chamber 15. The blocking method effectively limits more sample material from entering chamber 15 and thus provides a means for creating a predetermined fixed volume of sampled metal without adding additional heat absorbing components.

BRIEF SUMMARY OF THE INVENTION

According to a first aspect of the present invention, a probe for insertion into molten metal to detect and measure particulates suspended therein using the electric sensing zone method includes a sealed inner tube of an electrically insulative material forming a molten metal receiving chamber. The tube includes at least one orifice proximate an insertion end of the probe to permit molten metal to flow into the chamber. A gas passageway extends out of the inner tube for connection to a vacuum source to create a pressure differential between the inside and outside of the inner tube for facilitating the flow of molten metal through the at least one orifice.

A first electrode extends into the chamber for engaging metal within the chamber and includes the gas passageway and at least one first elongate member having a first length and electrically connected to the gas passageway. A second electrode surrounds at least a portion of the inner tube for engaging molten metal outside of the chamber. The first and second electrodes are connectable to a measurement device for establishing a current path through the electrodes and passing through the at least one orifice and for measuring changes in the electrical potential between the electrodes produced by the passage of particulates entrained in the molten metal passing through the orifice. An outer sheath of heat resistant material surrounds at least a portion of the second electrode to provide thermal insulation therefor. A liquidus depressing material within the chamber for alloying with molten metal entering the chamber lowers the liquidus temperature of the molten metal in the chamber and permits a longer time period for detecting and measuring particulates in the molten metal.

At least one second elongate member is electrically connected to the gas passageway at a first end of the at least one second member and extends into the chamber for engaging metal within the chamber. A chill block is attached to a second end of the at least one second member. The at least one second member has a second length such that the chill block is spaced from the liquidus depressing material.

According to a second aspect of the present invention, a method detects and measures particulates suspended in molten metal using a probe. The probe includes a sealed inner tube of electrically insulated material for establishing a receiving chamber. An orifice permits molten metal to flow into the chamber. A first electrode extends into the chamber for engaging molten metal within the chamber and a second electrode surrounds at least a portion of the inner tube for engaging molten metal outside of the chamber. An outer sheath of heat resistant material surrounds at least a portion of the second electrode to provide thermal insulation therefor. A gas passageway extends out of the inner tube.

The method includes installing a liquidus depressing material within the chamber. A chill block is connected to the first electrode. The first and second electrodes are connected to a measurement device, such that the first electrode includes the gas passageway, at least one first wire which extends from the gas passageway and into the chamber and at least one second wire which extends from the gas passageway and into the chamber. The at least one second wire is shorter than the at least one first wire. The chill block is attached to the at least one second wire.

The gas passageway is connected to a vacuum source. The probe is installed in molten metal such that molten metal flows through the orifice and into the chamber. The measurement device establishes a current path through the electrodes and passing through the orifice. Changes are measured in the electrical potential between the electrodes produced by the passage of particulates entrained in the molten metal passing through the orifice.

BRIEF DESCRIPTION OF THE SEVERAL VIEWS OF THE DRAWINGS

The following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
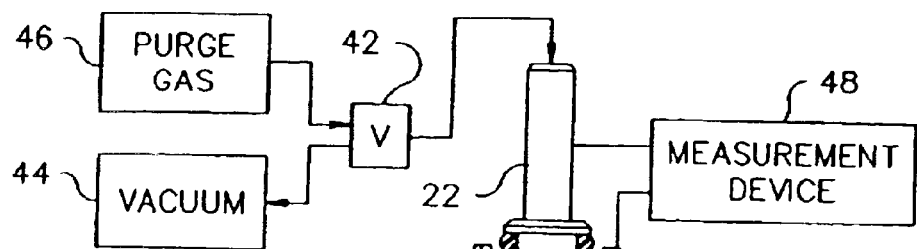
FIG. 1 is a cross-sectional, elevational view of a prior art probe.
Figure 1:
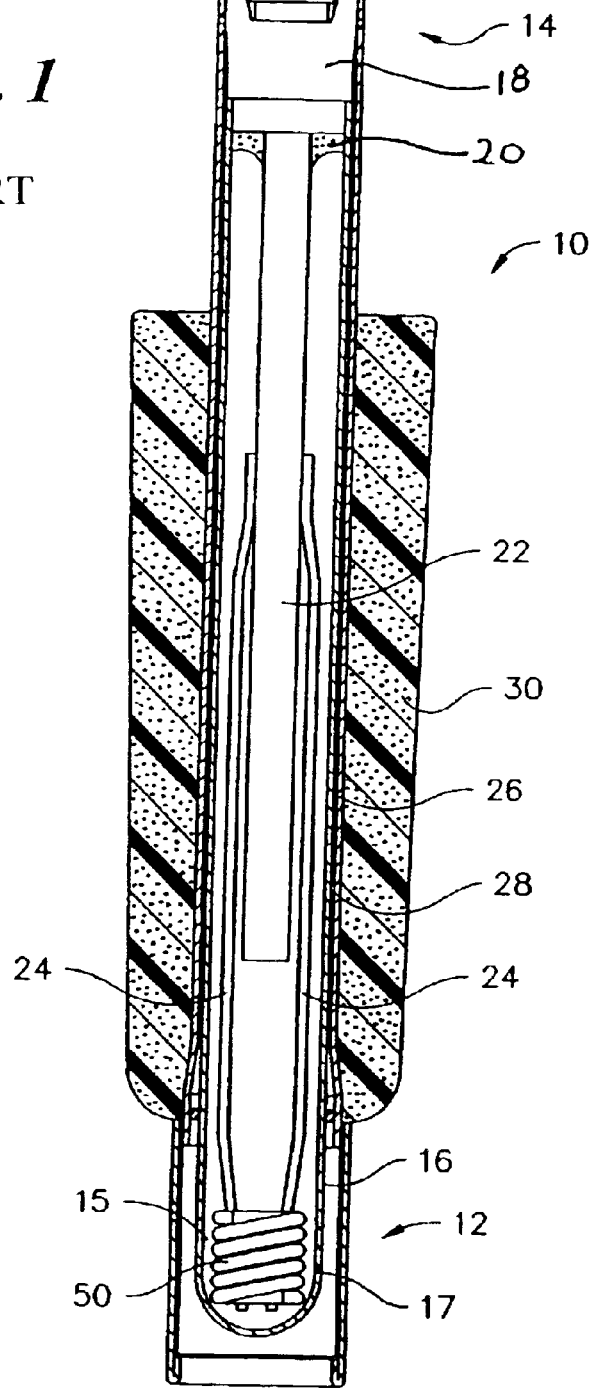
Figure 2:
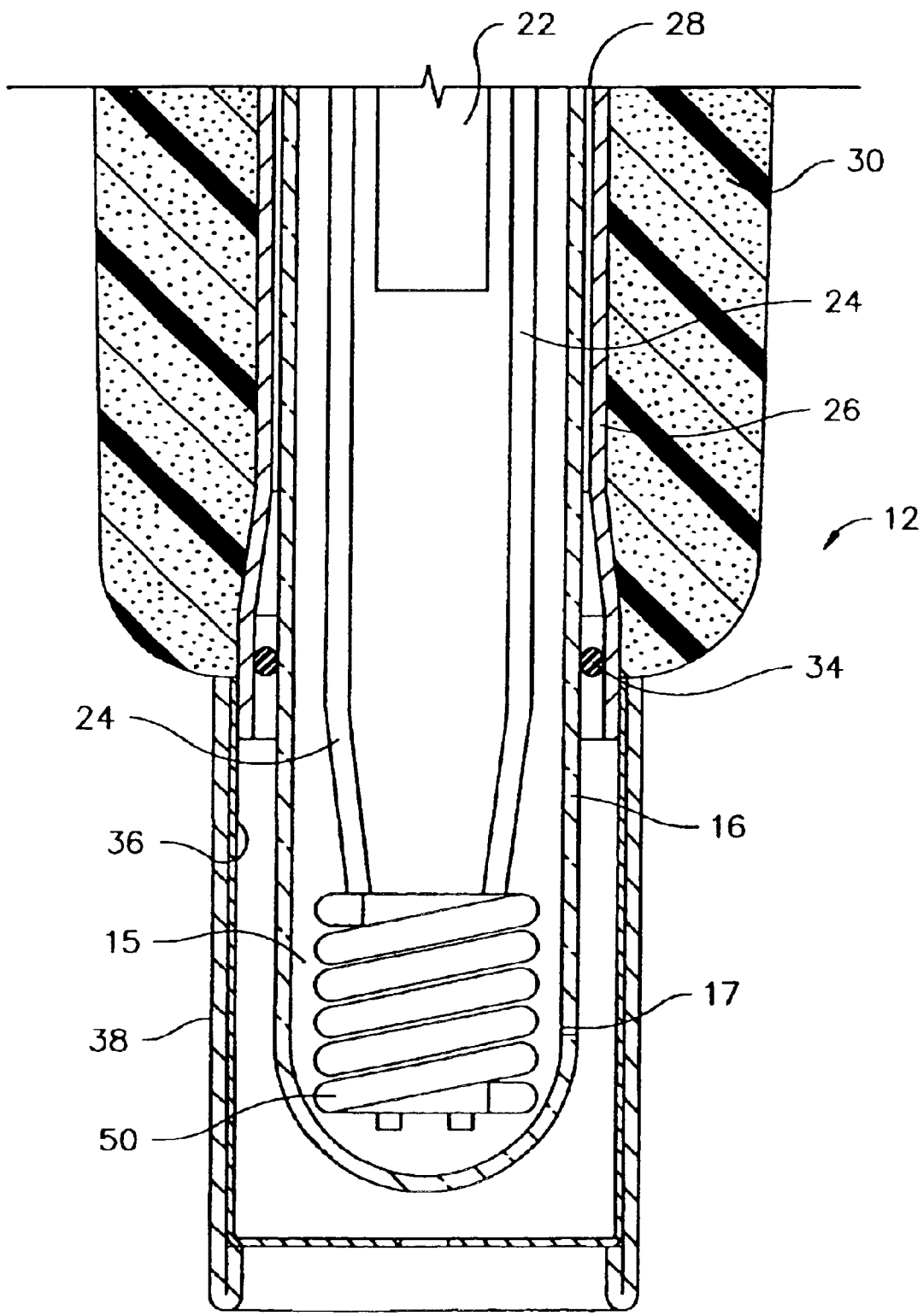
FIG. 2 is an enlarged cross-sectional elevational view of the insertion end of the probe shown in FIG. 1.
Figure 3:
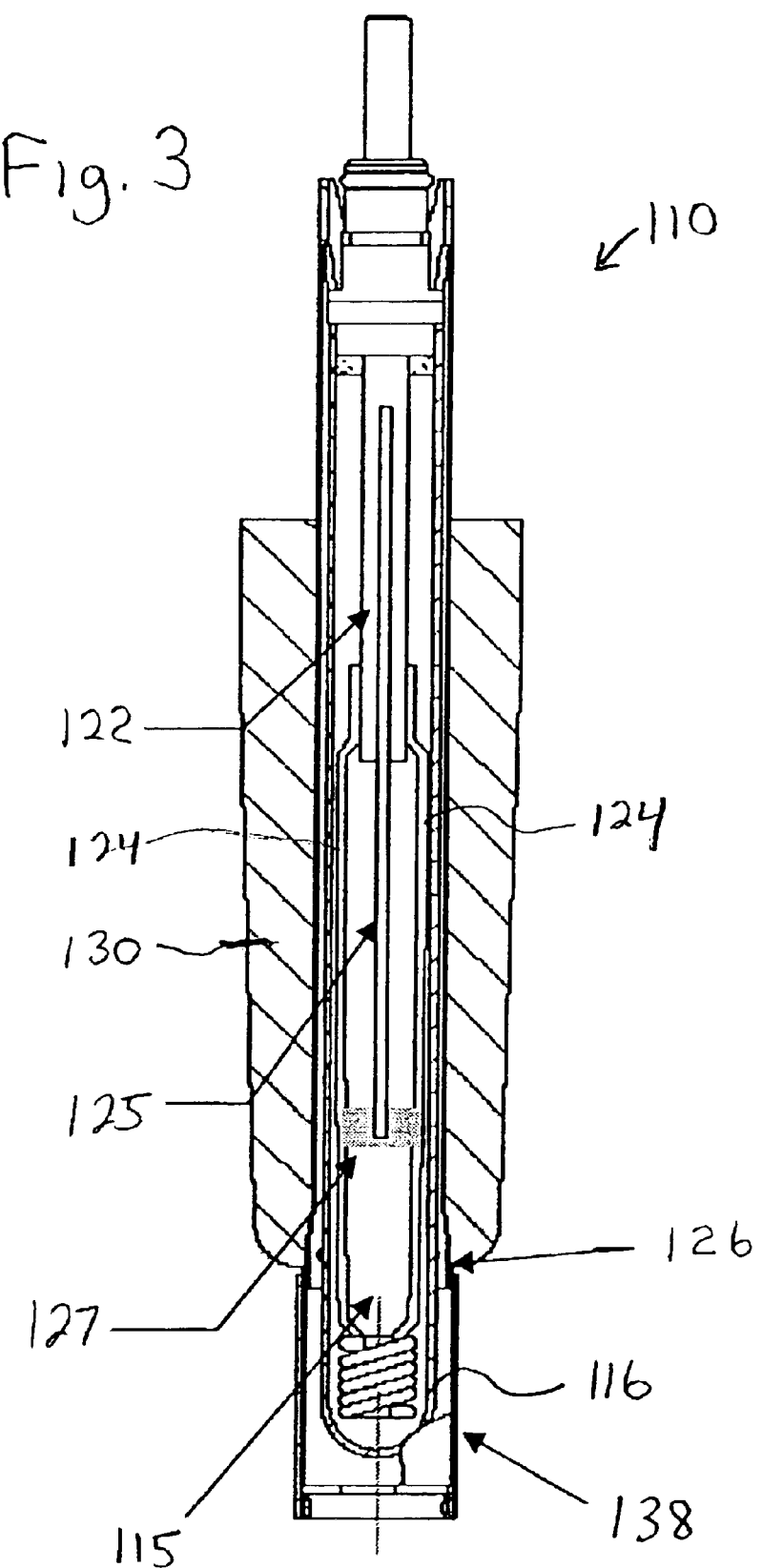
FIG. 3 is a cross sectional elevational view of a preferred embodiment of an improved probe in accordance with the present invention.

While the prior art probe 10 as shown in FIGS. 1 and 2 functions adequately, it suffers from at least one drawback which is overcome by the present invention. As discussed above, during operation, a vacuum pressure is created within in the receiving chamber 15 which results in molten metal flowing into the chamber through the orifice 17. The passage of entrained material through the orifice 17 is detected by changes in the current flow as discussed above. As the molten metal accumulates in the chamber 15, the molten metal will eventually block the distal end of the gas passageway 22 thereby effectively preventing continuation of the vacuum pressure in the chamber 15, stopping the flow of molten metal into the chamber 15 and precluding any further effective measurement of inclusions. Because of the structure of the prior art probe 10, the precise amount of molten metal present in the chamber 15 at the time that the gas passageway 22 is fully blocked is not certain and varies based upon metal fluidics, orifice size and other factors. The present invention overcomes the problems associated with the prior art probe by permitting a more precisely defined cut off time for measuring particulates in the molten metal which is based upon a more precisely controlled volume of molten metal in the chamber to provide for a more user friendly, more accurate measurement of inclusions. FIG. 3 illustrates an improved probe 110 in accordance with the present invention for detecting and measuring particulates suspended in molten metal. The improved probe 110 is substantially the same as the probe 10 described above in connection with FIGS. 1 and 2 with some noted differences. Accordingly, the foregoing description relates only to the structural and functional differences between the present probe 110 and the prior art probe 10.

Referring now to FIG. 3, the first principal difference involves the gas passageway 122 which, in the present embodiment, is considerably shorter than the gas passageway 22 of the prior art probe 10. As shown in FIG. 3, the gas passageway 122 extends less than half-way along the length of the inner tube 116. By shortening the length of the gas passageway 122 considerable additional molten metal may be permitted to be accumulated within the molten metal receiving chamber 115 without the distal end of the gas passageway 122 being blocked to thereby cut off the vacuum pressure within the chamber 115. The first pair of wires 124 are preferably connected to the gas passageway 122 at the distal end of the gas passageway.

The second principal difference involves the use of at least one and preferably a pair of second elongated cylindrical members or wires 125 which are securely connected (mechanically and electrically) at a first end thereof to the gas passageway 122, preferably by welding, brazing, soldering or the like. The second wires 125, which have a second length that is shorter than a first length of the first pair of wires 124, extend into the chamber 115 along the interior of the inner tube 116 for engaging metal within the chamber 115. The second pair of wires 125 terminate at a predetermined location which is spaced from the closed end of the tube 116 by a predetermined distance. The second pair of wires 125 are, formed of an electrically conductive material and, in combination with the gas passageway 122 and the first pair of generally cylindrical members or wires 124 form a first electrode extending into the molten metal receiving chamber 115. A generally cylindrical metal chill block 127 is secured (mechanically and electrically) to the distal or second ends of the second pair of wires 125, such that the chill block 127 is spaced from the liquidus depressing material in the chamber 115. The chill block 127 is made of a standard chill material well known to those of ordinary skill in the art.

With the exception of the shortened gas passageway 122, the addition of the second pair of wires 125 and the addition of the chill block 127, the probe 110 is the same as the probe 10 as described above in connection with FIGS. 1 and 2. In use, the probe 110 is connected to a vacuum source and purge gas source through a valve in the same manner as described above in connection with the prior art probe 10. The probe 110 is also connected to a measurement device 48 in the same manner as described above. Initially, the probe 110 is inserted into molten metal and the same detection and measuring process occurs as described above in connection with the prior art probe 10. During the initial measurement process, a constant current in supplied across the orifice between the first electrode and the second electrode 126. Initially, molten metal entering the chamber 115 makes electrical contact between the two electrodes over only the first pair of wires 124. Thus, the resistance of the circuit is influenced only by the resistance of the single pair of wires 124 by a known and measurable amount. As the chamber 115 continues to fill with the molten metal, the metal will eventually contact the metal chill block 127. At this time, the resistance in the constant current circuit changes due to a drop in resistance of the circuit because of the addition of the second pair of wires 125 which will change the resistance within the circuit. The drop in resistance results in a temporary transient surge within the circuit which is a measurable signal that can be detected within the measurement device. Because the location of the metal chill block 127 within the inner tube 116 is known, the measurement device 48 will know the precise volume of metal in the chamber 115 at the time the molten metal first comes into contact with the chill block 127. This will provide the measurement device with additional information necessary for determining a more precise count of the inclusions within a particular precise volume of the molten metal. In addition, the molten metal contacting the chill block 127 provides a more precise and easily determinable signal to effectively end the taking of measurements resulting in a more dependable analysis of the inclusions within the molten metal.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. In a probe for insertion into molten metal to detect and measure particulates suspended therein using the electric sensing zone method, the probe comprising:

a sealed inner tube of an electrically insulative material forming a molten metal receiving chamber, the tube including at least one orifice proximate an insertion end of the probe to permit molten metal to flow into the chamber;

a gas passageway extending out of the inner tube for connection to a vacuum source to create a pressure differential between the inside and outside of the inner tube for facilitating the flow of molten metal through the at least one orifice;

a first electrode extending into the chamber for engaging metal within the chamber, the first electrode including the gas passageway and at least one first elongate member having a first length and electrically connected to the gas passageway;

a second electrode surrounding at least a portion of the inner tube for engaging molten metal outside of the chamber, the first and second electrodes being connectable to a measurement device for establishing a current path through the electrodes and passing through the at least one orifice and for measuring changes in the electrical potential between the electrodes produced by the passage of particulates entrained in the molten metal passing through the orifice;

an outer sheath of heat resistant material surrounding at least a portion of the second electrode to provide thermal insulation therefor;

a liquidus depressing material within the chamber for alloying with molten metal entering the chamber to lower the liquidus temperature of the molten metal in the chamber and permit a longer time period for detecting and measuring particulates in the molten metal, an improvement comprising:

at least one second elongate member electrically connected to the gas passageway at a first end of the at least one second member and extending into the chamber for engaging metal within the chamber; and a chill block attached to a second end of the at least one second member, the at least one second member having a second length such that the chill block is spaced from the liquidus depressing material.

2. The probe of claim 1 wherein the second length is shorter than the first length.

3. The probe of claim 1 wherein the gas passageway extends less than half-way along the length of the inner tube.

4. The probe of claim 1 wherein the at least one first member is connected to a distal end of the gas passageway.

5. The probe of claim 1 wherein the gas passageway is initially connected to a source of purge gas for causing purge gas to flow into the chamber, at least during insertion of the probe into the molten metal, to prevent molten metal from flowing into the chamber.

6. The probe of claim 5 further comprising a valve for connecting the gas passageway to either the vacuum source or the purge gas source.

7. The probe of claim 1 wherein the gas passageway extends into the inner tube by a predetermined distance to establish the amount of metal which may enter the chamber.

8. The probe of claim 1 wherein the first electrode comprises the gas passageway, at least one first wire extending from the gas passageway and into the chamber and at least one second wire extending from the gas passageway and into the chamber.

9. The probe of claim 1 wherein the inner dimension of the second electrode is greater than the outer dimension of the inner tube to create an annular space there between.

10. The probe of claim 9 further comprising a spacer member positioned within the annular space proximate the insertion end of the second electrode.

11. A method for detecting and measuring particulates suspended in molten metal using a probe including a sealed inner tube of electrically insulated material for establishing a receiving chamber, the tube including an orifice to permit molten metal to flow into the chamber, a first electrode extending into the chamber for engaging molten metal within the chamber, a second electrode surrounding at least a portion of the inner tube for engaging molten metal outside of the chamber, an outer sheath of heat resistant material surrounding at least a portion of the second electrode to provide thermal insulation therefor, and a gas passageway extending out of the inner tube, the method comprising the steps of installing a liquidus depressing material within the chamber;

connecting a chill block to the first electrode;

connecting the first and second electrodes to a measurement device, wherein the first electrode includes the gas passageway, at least one first wire extending from the gas passageway and into the chamber and at least one second wire extending from the gas passageway and into the chamber, the at least one second wire being shorter than the at least one first wire, the chill block being attached to the at least one second wire;

connecting the gas passageway to a vacuum source;

installing the probe in molten metal such that molten metal flows through the orifice and into the chamber;

the measurement device establishing a current path through the electrodes and passing through the orifice; and measuring changes in the electrical potential between the electrodes produced by the passage of particulates entrained in the molten metal passing through the orifice.

\* \* \* \* \*